(12) United States Patent  
Khalili

(10) Patent No.: US 8,162,989 B2
(45) Date of Patent: Apr. 24, 2012

(54) ORTHOPEDIC ROD SYSTEM

(75) Inventor: Farid Bruce Khalili, Briar Cliff Manor, NY (US)

(73) Assignee: Altus Partners, LLC, Newtown Square, PA (US)

( * ) Notice: Subject to any disclaimer, the term of this patent is extended or adjusted under 35 U.S.C. 154(b) by 1146 days.

(21) Appl. No.: 10/693,698

(22) Filed: Oct. 27, 2003

(65) Prior Publication Data

US 2006/0025767 A1 Feb. 2, 2006

Related U.S. Application Data

(60) Provisional application No. 60/423,168, filed on Nov. 4, 2002, provisional application No. 60/479,822, filed on Jun. 20, 2003.

(51) Int. Cl.
*A61B 17/70* (2006.01)
(52) U.S. Cl. ....................................... 606/266
(58) Field of Classification Search .............. 606/61, 606/72–73
See application file for complete search history.

(56) References Cited

U.S. PATENT DOCUMENTS

| | | | | |
|---|---|---|---|---|
| 5,474,555 A * | 12/1995 | Puno et al. | 606/73 |
| 5,496,321 A * | 3/1996 | Puno et al. | 606/61 |
| 5,683,390 A * | 11/1997 | Metz-Stavenhagen et al. | 606/61 |
| 5,879,350 A * | 3/1999 | Sherman et al. | 606/61 |
| 6,063,090 A * | 5/2000 | Schlapfer | 606/270 |
| 6,090,111 A * | 7/2000 | Nichols | 606/61 |
| 6,110,172 A * | 8/2000 | Jackson | 606/61 |
| 6,248,105 B1 * | 6/2001 | Schlapfer et al. | 606/61 |
| 6,251,112 B1 * | 6/2001 | Jackson | 606/61 |
| 6,254,602 B1 * | 7/2001 | Justis | 606/61 |
| 6,273,888 B1 * | 8/2001 | Justis | 606/61 |
| 6,280,442 B1 * | 8/2001 | Barker et al. | 606/60 |
| 6,355,040 B1 * | 3/2002 | Richelsoph et al. | 606/61 |
| 6,440,132 B1 * | 8/2002 | Jackson | 606/61 |
| 6,443,953 B1 * | 9/2002 | Perra et al. | 606/61 |
| 6,471,705 B1 * | 10/2002 | Biedermann et al. | 606/61 |
| 6,565,565 B1 * | 5/2003 | Yuan et al. | 606/61 |
| 6,565,566 B1 * | 5/2003 | Wagner et al. | 606/61 |
| 6,652,526 B1 * | 11/2003 | Arafiles | 606/61 |
| 6,689,133 B2 * | 2/2004 | Morrison et al. | 606/71 |
| 6,755,829 B1 * | 6/2004 | Bono et al. | 606/61 |
| 7,081,117 B2 | 7/2006 | Bono et al. | |
| 7,322,981 B2 * | 1/2008 | Jackson | 606/266 |
| 7,338,491 B2 * | 3/2008 | Baker et al. | 606/308 |
| 7,559,943 B2 * | 7/2009 | Mujwid | 606/266 |
| 7,776,067 B2 * | 8/2010 | Jackson | 606/246 |
| 7,857,834 B2 * | 12/2010 | Boschert | 606/269 |
| 7,967,850 B2 * | 6/2011 | Jackson | 606/301 |
| 8,092,494 B2 * | 1/2012 | Butler et al. | 606/246 |
| 2001/0047173 A1 * | 11/2001 | Schlapfer et al. | 606/72 |
| 2002/0120272 A1 * | 8/2002 | Yuan et al. | 606/61 |
| 2004/0116929 A1 * | 6/2004 | Barker et al. | 606/61 |
| 2004/0143265 A1 * | 7/2004 | Landry et al. | 606/61 |

\* cited by examiner

*Primary Examiner* — Eduardo C Robert
*Assistant Examiner* — Mary Hoffman
(74) *Attorney, Agent, or Firm* — Matthew B. Dernier; Gibson & Dernier LLP

(57) ABSTRACT

A tulip-shaped rod-receiving member in a spinal rod system is provided with a transverse slot accessible from the top of the tulip member for placing the rod therein until the rod seats. A locking assembly includes a cap having inclined surfaces that cooperate with inclined surfaces on the rod-receiving member to lock and bias inwardly the rod-receiving member relative to the cap. A novel seating ring is provided for the bone screw to be supported in the tulip in a manner that maximizes support and optimizes axial alignment of forces.

11 Claims, 7 Drawing Sheets

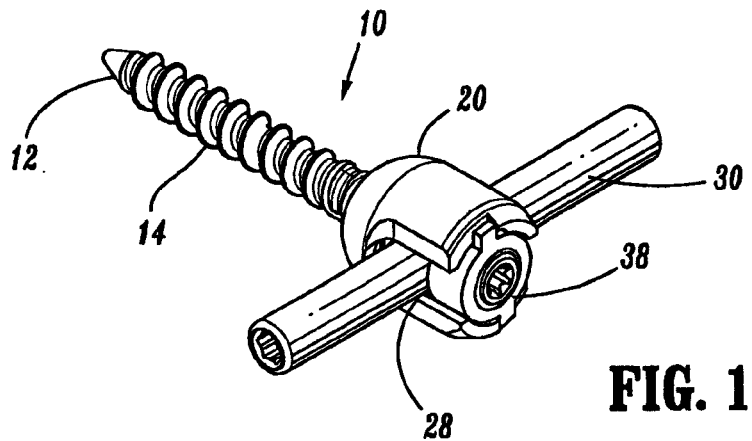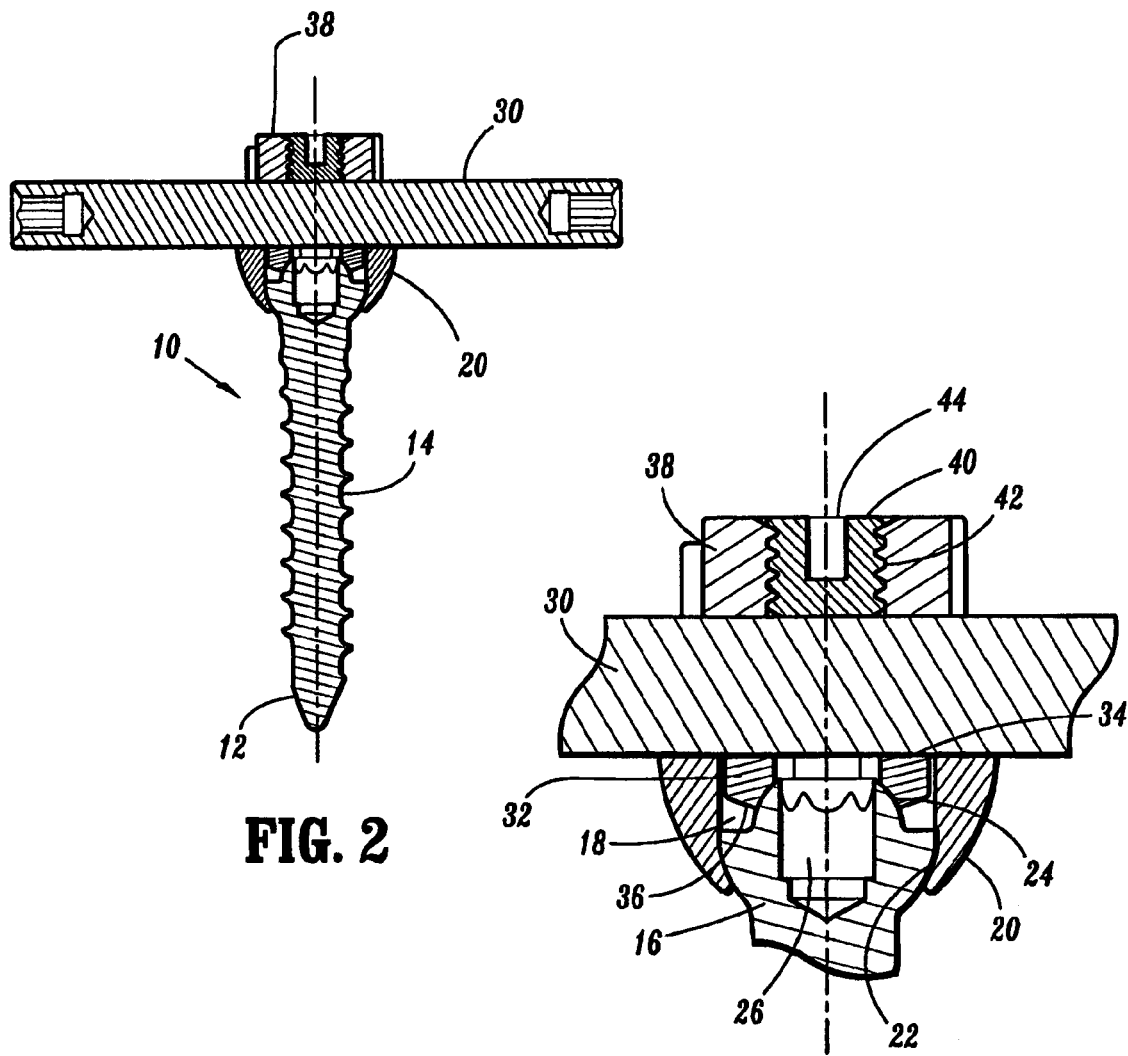
FIG. 1
FIG. 2
FIG. 3

ORTHOPEDIC ROD SYSTEM

RELATED APPLICATIONS

This application is related to, and claims priority from, the following earlier-filed U.S. Provisional Patent Applications: (Ser. Nos.) 60/423,168 (filed 4 Nov. 2002); 60/479,822 (filed 20 Jun. 2003). Each is incorporated herein by reference.

TECHNICAL FIELD

The present invention relates to orthopedic implantable devices, related systems, and associated methods of use and, more particularly, to a pedicle screw and rod system and associated method for joining two or more bone segments, such as vertebrae.

BACKGROUND OF THE INVENTION

Pedicle screw systems used for fastening spinal rod systems to the pedicle region of two or more vertebral bodies exist in a variety of forms. Successive designs have strived to attain optimal levels of performance, costs, and ease of use. Some known pedicle screw systems provide a locking cap that is threadingly received into a holding sleeve. To lock the pedicle screw relative to the rod the cap is placed into the sleeve (the rod positioned therebetween), and the cap is tightened. This task is difficult since the surgeon must manipulate and tighten the cap while holding the pedicle screw and rod at a particular desired angle. Associated problems are difficulty of installation and cross-threading.

Alternative designs include cams or circular ramps to reduce the number of turns required to lock the cap. Such designs require costly and precise tolerances and are difficult to use during surgery.

OBJECTS AND SUMMARY OF THE INVENTION

It is an object of the present invention to provide pedicle screw and rod system that overcomes the above-described shortcomings associated with prior, known designs.

These and other objects are described below or inherent with respect to the present invention.

In one aspect of the present invention, a tulip-shaped rod-receiving member is provided with a transverse slot accessible from the top of the tulip member for placing the rod therein until the rod seats. A locking assembly includes a cap having transversely aligned wings that are passed through the slot and then, as the cap is rotated, positioned into dove-tail like grooves that prevent the cap from being backed out. A set screw positioned through the cap is tightened against the rod applying downward force thereto while transmitting upward force to the tulip via the dovetail groove. The groove has angled sides that cooperate with angled sides of the cap wings so that as force is increased, the angle sides slide relative to each other in a manner that applies closing force to the tulip, rather than spreading force.

In another embodiment of the present invention, a tulip-shaped receiving member with a slot for receiving a rod has at least two inverted shoulders that have downwardly-facing contact surfaces that incline upwardly in a direction radially outwardly from a center axis of the tulip. A locking cap is provided having at least two shoulders that have upwardly-facing contact surfaces that incline upwardly in a direction radially outwardly from a center axis of the cap, so that the respective inclined surfaces of the cap and the tulip matingly engage. Thus, when a tightening screw is advanced through a central opening in the cap to exert pressure on a rod positioned through the tulip-slot, the reaction force transmitted to the screw is transferred to the inclined surfaces causing the walls of the tulip to be biased radially inwardly as the rod is locked increasingly.

Another aspect of the present invention, specifically directed to the embodiments described below relating to multi-axis systems, provides that due to the novel design of a seated bone screw, maximum alignment of locking forces can be achieved with minimal sizing of a screw head.

BRIEF DESCRIPTION OF THE DRAWINGS

FIG. 1 is a perspective view of a pedicle screw and rod system according to a preferred embodiment of the present invention.

FIG. 2 is a side, cross-sectional view of the pedicle screw and rod system according to FIG. 1.

FIG. 3 is a partial, cross-sectional view of the pedicle screw and rod system according to FIG. 1.

DESCRIPTION OF THE PREFERRED EMBODIMENTS

Figure 4:
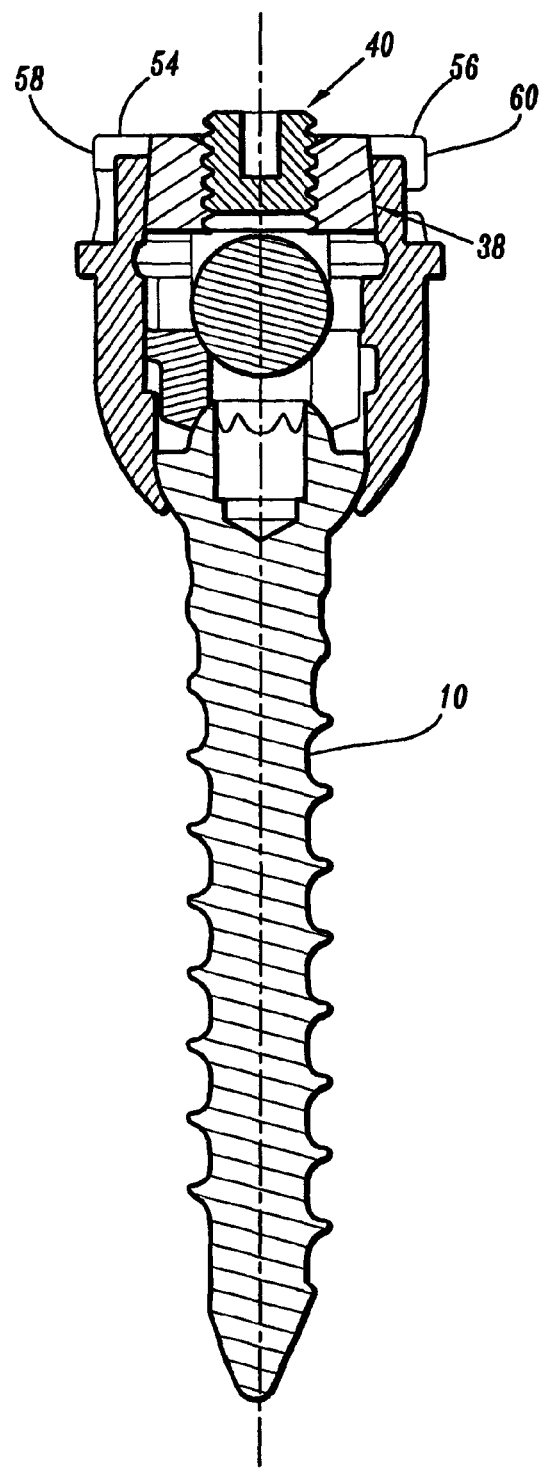
FIG. 4 is a partial, cross-sectional view of the pedicle screw and rod system according to FIG. 1, shown in the un-locked position and viewed at 90 degrees with respect to FIG. 3.

Referring to FIGS. 1-3, a pedicle screw (10) according to the present invention includes a first end (12) adapted to be driven into bone, a threaded intermediate portion (14), and a head (16) having a semicircular profile. The screw (10) is positioned through a central opening (18) in a rod-receiving cup (20). The cup (20) has a lower, conical interior surface (22) that the head (16) pivotally rests in. The head (16) also includes a dome top (24) and a driver-engaging socket (26).

The cup (20) has two opposed slots (28) forming a yoke through which a rod (30) is received. A lower surface (36) of a seat element (32) rests in slideable contact with the dome top (24) of the screw head (16). The upper surface (34) of the seat element (32) contacts the rod (30). An upper cap (38) is received in the upper end of the cup (20) above the rod (30). A locking threaded screw (40) having a tool engaging socket

(44) is tightened through a central, threaded opening (42) in the cap (38) so that the locking screw (40) contacts the rod (30).

Figures 5, 6:
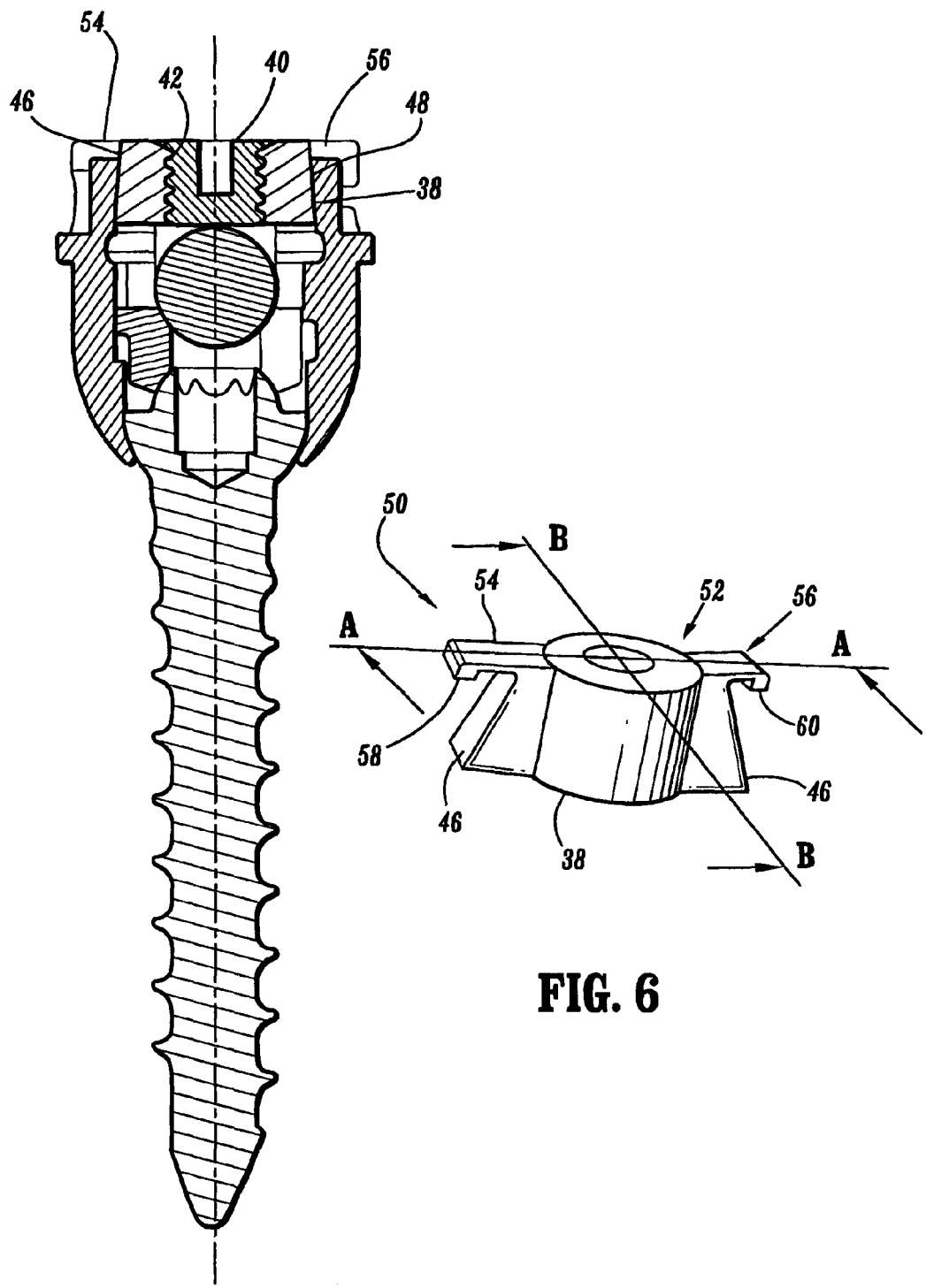
FIG. 5 is a partial, cross-sectional view of the pedicle screw and rod system according to FIG. 1, shown in the locked position and viewed at 90 degrees with respect to FIG. 3.
FIG. 6 is a schematic, perspective view of a component of the pedicle screw and rod system according to FIG. 1, having exaggerated dimensions for illustrative purposes.

As the locking screw (40) is tightened, it is driven against the rod, thereby causing upward displacement of the cap (38). Because the cap (38) is constrained against upward movement by the cup (20), and the rod (30) and seat element (32) are constrained against downward movement by the screw head (16), which bottoms out against the inner surface (22) of the cup (20), these components are all locked relative to each other by turning of the locking screw (40). FIG. 4 illustrates an unlocked condition, and FIG. 5 illustrates a locked condition. These modes facilitate angular selection and locking of the pedicle screw (10).

The cap (38) is constrained against upward movement by the cup (20) due to its upwardly tapering ramps (46), which correspond to an inverted, matching inner wall (48) of the cup (20) interior, as shown in FIGS. 4-5. The cap (38) has opposed, radially extending wings (50, 52) with top arms, (54, 56) having downwardly-extending ends (58, 60) and ramps (46).

In order to more clearly illustrate the locking features of the cap (38), a schematic illustration of the cap (38) is shown in FIG. 6 having exaggerated dimensions. The wings (50, 52) can be aligned within the yoke formed by the slots (28), and then turned ninety degrees to position the ramps (46) into engagement with the cup inner wall (48). The downwardly-extending ends (58, 60) of the arms (54, 56) engage the outside surface of the cup (20) to prevent radially outward deflection or deformation of the cup (20) as the locking screw (40) is advanced against the rod (30) causing the cap (38) to be biased upwardly against the tapered inner surface (48) of the cup (20).

This design allows loose retention of the components relative to the rod so a surgeon can easily make adjustments. It also enables superior performance without the need for costly high tolerancing.

Figure 7:
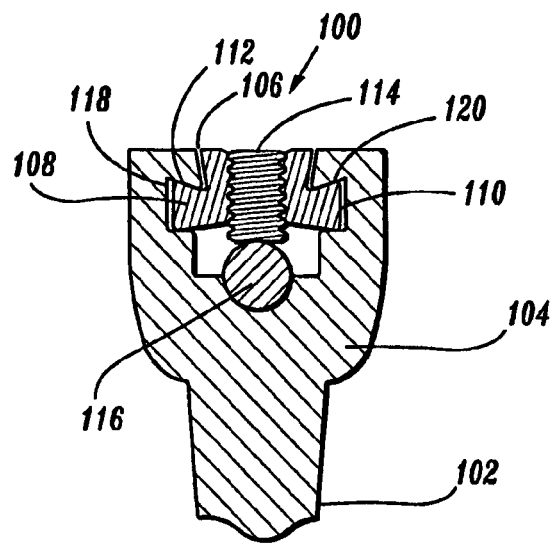
FIG. 7 is a cross-sectional view of a pedicle screw and rod system according to a second embodiment of the present invention.

A second embodiment of the present invention, shown in FIG. 7, is directed to fixed axis pedicle screw (100) having a shaft (102), such as a threaded shaft, and a head (104) integrally formed. The head (104) has a slotted opening (106) similar to that described above with respect to the first embodiment of the present invention designed to cooperate with a cap member (108) having wings (110) with angled surfaces (112) of the type described with respect to the first embodiment. A set screw (114) is designed to apply downward force to a rod (116) as described above with respect to the first embodiment: The wings (110) are passed through the slot (116) and then, as the cap (108) is rotated, positioned into dove-tail like grooves (118) that prevent the cap from being backed out. A set screw (114) positioned through the cap (108) is tightened against the rod (116) applying downward force thereto while transmitting upward force to the tulip via the dovetail groove (118). The groove (118) has angled sides (120) that cooperate with angled sides (112) of the cap wings so that as force is increased, the angle sides (120, 112) slide relative to each other in a manner that applies closing force to the tulip, rather than spreading force.

Figure 8:
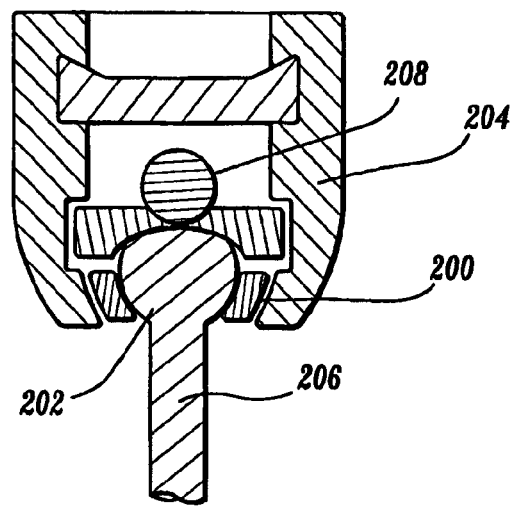
FIG. 8 is a schematic, cross-sectional view of a pedicle screw and rod system according to a third embodiment of the present invention.

A third embodiment of the present invention as shown schematically in FIG. 8 is essentially similar to the first embodiment described herein, except that it utilizes a seat sleeve (200) for seating the screw head (202) relative to the cup (204) or tulip. In this embodiment, the use of the seat sleeve (200) enables a smaller screw head (202) to be used, while enabling a wide range of angular positioning of the screw (206) relative to the cup (204) that would otherwise be unattainable without the seat sleeve (200). The sleeve (200) retains the screw (206) in an opening of the cup (204) that the screw (206) would otherwise fall through. As illustrated with respect to FIGS. 9-10, the third embodiment of the present invention, represented schematically in FIG. 9, enables the center (210) of the screw head (214) to remain vertically aligned with the center (212) of the rod (208). Referring to the schematic of the PRIOR ART in FIG. 10, the size of the screw head (300) relative to the cup (302) and its opening causes the center (304) of the head (300) to move out of vertical alignment with the center (306) of the rod by a distance "a". The superior alignment of the centers of the rod and the screw head achieved by the present invention distributes loads more equally within the cup, on the supporting structures, through the rod, and finally to the ramped surfaces of the cup dovetail groove and the cap angled surfaces. This relatively even stress distribution and efficient use of existing forces internal to the system provide superior performance and locking of the screw relative to the rod assembly.

Figure 9:
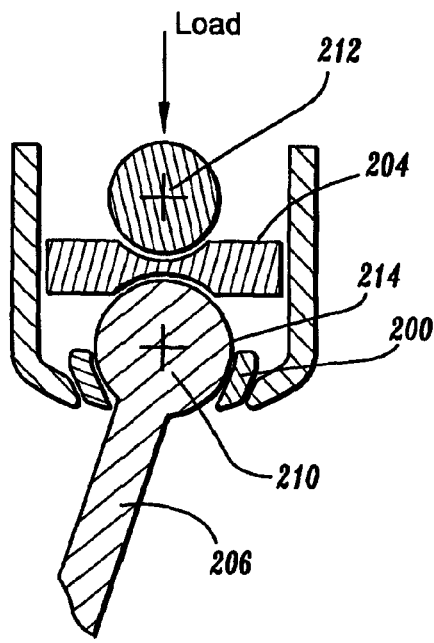
FIG. 9 is a schematic, cross-sectional view of a pedicle screw and rod system according to the third embodiment of the present invention.
Figure 10:
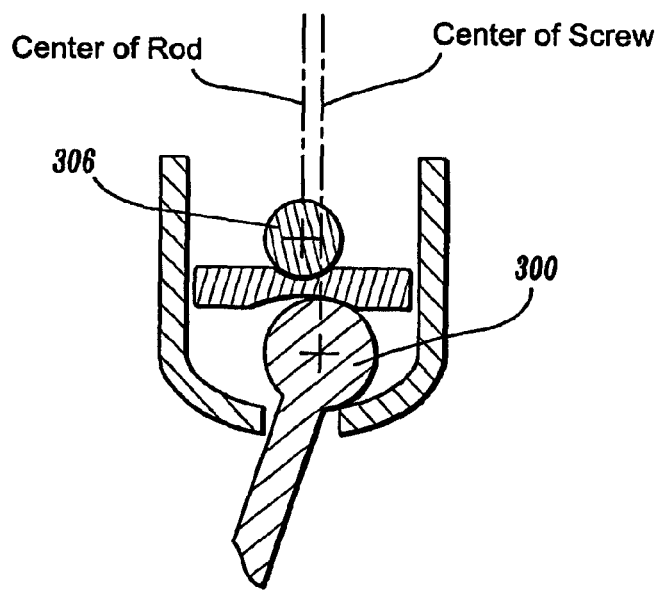
FIG. 10 is a schematic, cross-sectional view of a prior art pedicle screw and rod system.
Figure 11:
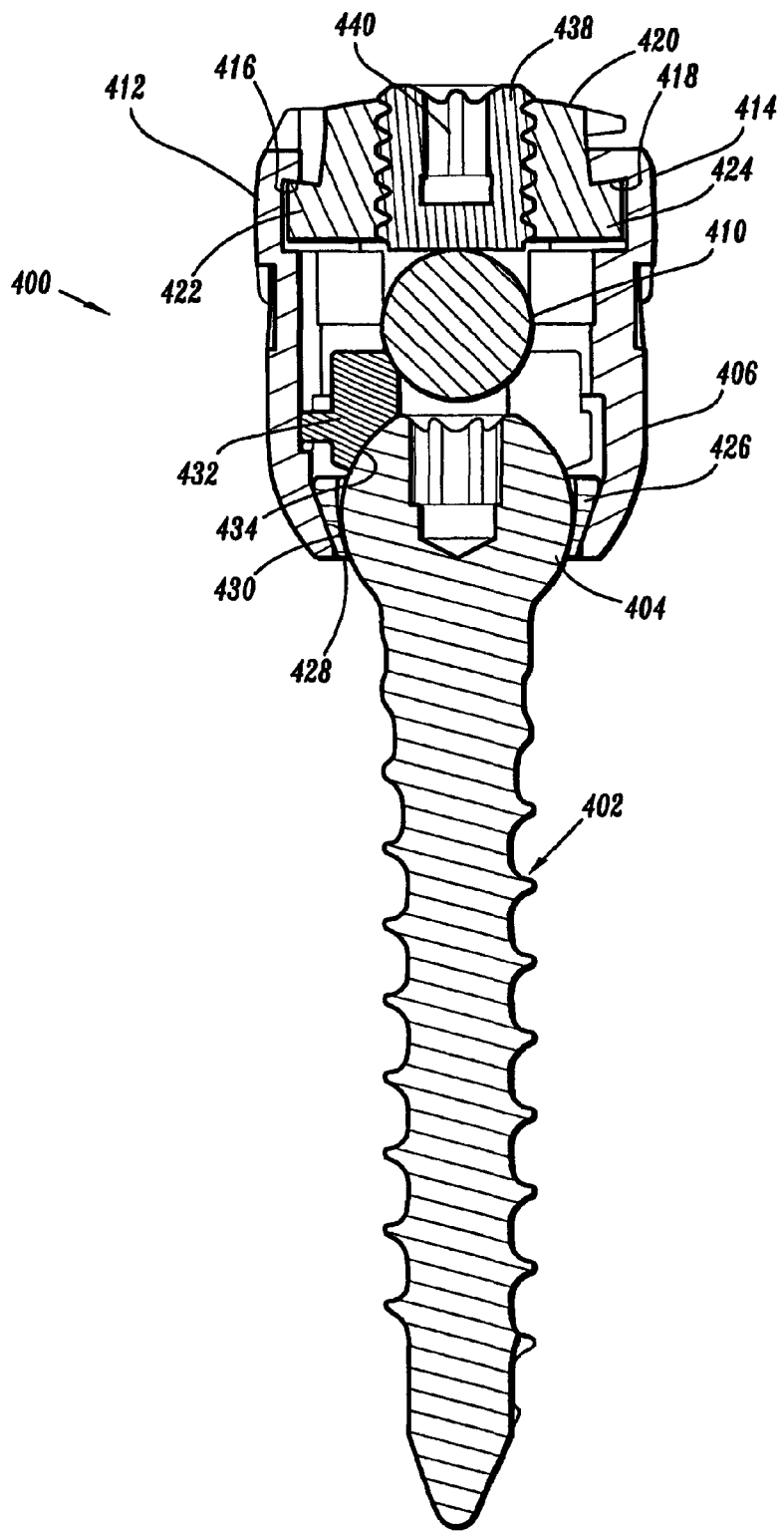
FIG. 11 is a front, cross-sectional view of a pedicle screw and rod system according to the third embodiment of the present invention.
Figure 12A:
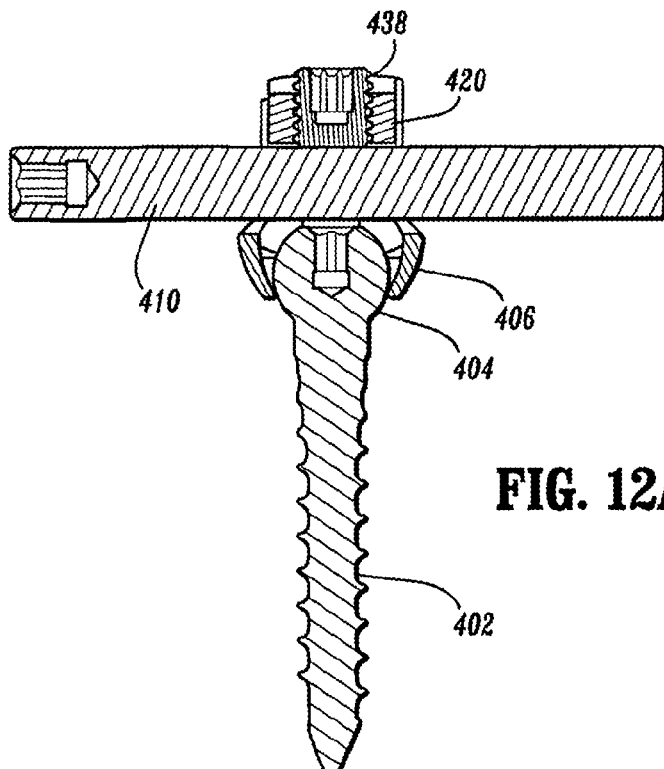
FIGS. 12A and 12B are partial, side, cross-sectional views of a pedicle screw and rod system according to FIG. 11.
Figure 12B:
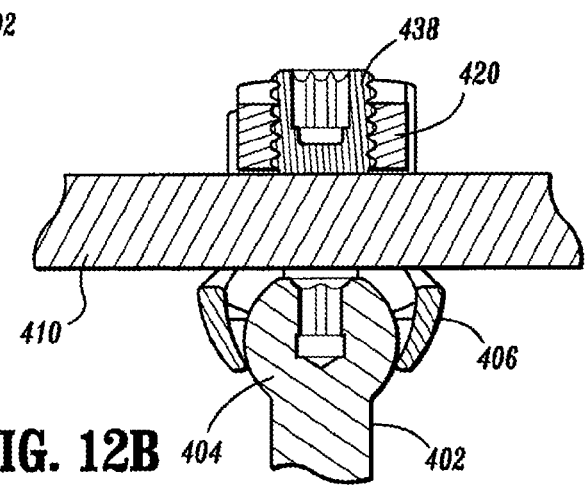
Figure 13:
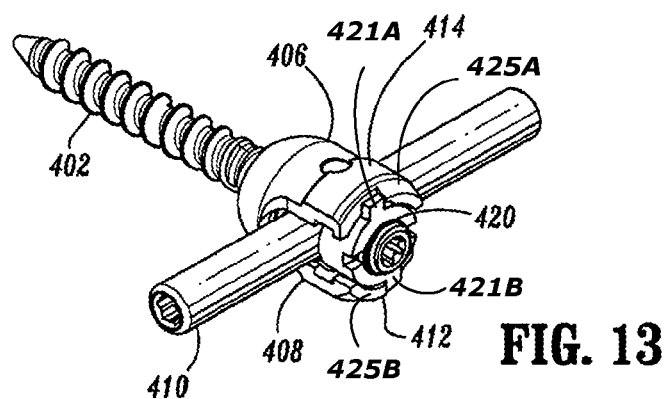
FIG. 13 is a perspective view of a pedicle screw and rod system according to FIG. 11.

With references to FIGS. 11-13, the third embodiment schematically represented in FIGS. 8-9 is illustrated by way of example in a pedicle screw and rod system (400). A pedicle screw (402) having a generally hemispherical head (404) suspended in a tulip (406) having a slot (408) for receiving an orthopedic rod such as a spinal rod (410). The tulip (406) has two sidewalls (412, 414) formed adjacent to the slot (408). Each sidewall (412; 414) has an inverted shoulder (416, 418) formed on the inner side of the sidewall. The inverted shoulders (416, 418) are inclined upwardly in a radially outward direction as shown. A cap (420) having two shoulders (422, 424), each being inclined upwardly in a radially outward direction as shown, is adapted to be positioned in the tulip (406) as shown. For optimal performance, it is preferable that the incline of the inverted shoulders (416, 418) be greater, or steeper, than the incline of the cap shoulders (422, 424), though they could also be approximately equal or less.

In use, the pedicle screw (402) is driven into bone while it is seated on a seat ring (426) that rests in a conically-tapering bottom opening (428) of the tulip (406). Because the ring (426) is a spacer between the screw head (404) and the tapered contact surface (430) inside the tulip (406), it enables a smaller profiled head (404) and screw thickness relative to the tulip opening (428), thus facilitating a wide range of angular adjustment of the pedicle screw (402) relative to the tulip (406). This is a significant improvement over known designs.

After the pedicle screw (402) is driven into the bone, a spacer cap (432) having a contoured lower contact surface (434) for engaging the screw head (404) and an upper contact surface (436) for engaging the rod (410) is positioned as shown in FIG. 11. The rod (410) is positioned, via the slot (408) to the position shown in FIG. 11, and the cap (420) is placed into the top of the tulip (406). The tulip (406) and pedicle screw (402) are manipulated to a relative angular orientation that is desired and held in such a position while the tightening screw (438) in the center of the cap (420) is advanced toward the rod (410). The tightening screw (438) is preferably threaded on its exterior and adapted to mate with threads on the interior of a hole in the center of the cap (420), as shown in FIG. 11. As the tightening screw (438) is advanced into contact with the rod (410) and further advanced, reaction forces transmitted from the rod (410) to the screw (438) are transmitted to the inclined shoulders (416, 418) of the sidewalls and the shoulders (422, 424) of the cap (420). The action of the inclined surfaces of the tulip shoulders (416, 418) and the cap shoulders (422, 424) being drawn against each other causes the sidewalls (412, 414) to be drawn radially inwardly, more tightly as the rod (410) is more tightly secured by the tightening screw (438). The tightening screw (428) is provided with a driving engagement feature (440) for applying turning torque. Because of the selected radius dimension of the screw head (404) and its point of suspension relative to the tulip (406), pivotal adjustment and locking of the pedicle screw (402) relative to the tulip (406) will always result in the force of the tightening screw (438) being directed along a line that intersects the center of the screw head (404).

In accordance with one or more embodiments, the cap 420 may include a generally cylindrical body having first and second opposing ends, 432A, 423B, an outer surface, and a bore extending through the first and second opposing ends 432A, 423B of the body along a central, longitudinal axis. The cap 420 may further include one or two shoulders 421A, 421B, disposed in opposing relationship when there are two such shoulders (as illustrated), and disposed proximate to the first end 423A of the body, and extending radially away, and circumferentially along, the outer surface of the body. As can best be seen in FIG. 13, at least portions of the shoulders 421A, 421B are sized and shaped to slide over, and overlie, respective portions of a lip of the tulip 406, at the periphery of the open end that receives the cap 420, by the rotation of the cap 420 about its longitudinal axis. The shoulders 422, 424 are sized and shaped to be: (i) received into the first and second slots (e.g., element 28 in FIG. 1), respectively, to positions adjacent to the opposing grooves (e.g., element 118 in FIG. 7), respectively, and (ii) slidingly received into the grooves 118 by rotation of the cap 420 about its longitudinal axis. As shoulders 422, 424 slide into the grooves 118 by rotation of the cap 420, the one or two shoulders 421A, 421B slide over the respective portions of the lip of the tulip 406 and abut respective associated tabs 425A, 425B, thereby operating to stop the cap 420 from rotating beyond a predetermined amount.

While the present invention has been described herein, various modification may be made without departing from the scope of the invention.

The invention claimed is:

1. An apparatus for bridging one or more vertebrae of a spine, the apparatus comprising:
    a fastener having a threaded shaft adapted to be driven into the vertebrae and a head at a proximal end of the shaft;
    a tulip having: (a) outer and inner walls defining opposing, and generally circularly open, first and second ends, (b) opposing first and second slots extending from the open first end toward the open second end, and (c) first and second grooves, each extending in opposing relation to one another along the inner wall from at least one of the first and second slots toward the other of the first and second slots, wherein: (i) the head of the fastener is retained within the tulip and proximate to the second end thereof, with the threaded shaft extending out of the tulip through the second opening thereof, and (ii) the opposing first and second slots are sized and shaped to receive a rod therethrough in a transverse orientation with respect to the threaded shaft of the fastener, such that the rod passes over the head; and
    a cap including: (a) a generally cylindrical body having first and second opposing ends, an outer surface, and a bore extending through the first and second opposing ends of the body along a central, longitudinal axis, (b) first and second shoulders disposed in opposing relationship to one another proximate to the first end of the body, and extending radially away, and circumferentially along, the outer surface of the body, (c) third and fourth shoulders disposed in an opposing relationship proximate to the second end of the body, and extending radially away, and circumferentially along, the outer surface of the body, wherein:
        the third and fourth shoulders are sized and shaped to be: (i) received into the first and second slots, respectively, to positions adjacent to the first and second grooves, respectively, and (ii) slidingly received into the first and second grooves by rotation of the cap about the longitudinal axis; and
        at least portions of the first and second shoulders are sized and shaped to slide over, and overlie, respective portions of a lip of the tulip at the periphery of the first open end of the tulip by the rotation of the cap about the longitudinal axis.

2. The apparatus of claim 1, wherein the cap includes no further shoulders beyond the first, second, third and fourth shoulders.

3. The apparatus of claim 1, wherein at least one of the first and second shoulders operate to stop the cap from rotating beyond a predetermined amount by bearing against an associated tab located at the lip of the tulip.

4. The apparatus of claim 3, wherein at least one of the first and second shoulders operate to stop the cap from rotating beyond the predetermined amount by bearing against an associated tab located at the lip of the tulip.

5. The apparatus of claim 1, further comprising a screw operating to thread into the bore of the cap, to urge the rod toward the second end of the tulip, and to tighten such that the rod, the head of the fastener, and the tulip are rigidly fixed and locked into position.

6. The apparatus of claim 5, further comprising a seat cap having first and second opposing surfaces disposed within the tulip, the first surface being oriented toward the first end of the tulip and operating to engage the rod, and the second surface being oriented toward the second end of the tulip and operating to permit sliding engagement with, and articulation of, the head when the screw is not tight.

7. The apparatus of claim 6, wherein a surface of the head that engages the second surface of the seat cap includes a generally dome-shaped contour, and the second surface of the seat cap includes a complementary contour in a manner permitting sliding articulation of the head within the tulip when the screw is not tight.

8. The apparatus of claim 7, wherein the first surface of the seat cap includes a U-shaped contour that complements and engages a contour of the rod in a manner permitting sliding and rotational articulation of the rod within the tulip when the screw is not tight.

9. The apparatus of claim 8, further comprising a seat ring having an annular configuration defined by inside and outside surfaces and opposing first and second open ends, the inside surface being sized and shaped to receive and permit articulation of the head when the screw is not tight, the second open end having a diameter sufficiently large to permit the threaded shaft to extend therethrough but not sufficiently large to permit the head to pass therethrough, and an outside surface being sized and shaped to engage the inner wall of, and prevent the head from extending through, the second open end of the tulip.

10. The apparatus of claim 9, wherein:
    the inner wall of the tulip includes a conical surface formed annularly about the open second end thereof; and
    the outside surface of the seat ring is sized and shaped to slidingly engage the conical surface and permit articulation of the head of the fastener when the screw is not tight.

11. The apparatus of claim 10, wherein tightening the screw into the bore of the cap causes: (i) a distal end of the screw to engage and urge the rod against the first surface of the seat cap; (ii) the second surface of the seat cap to engage and urge the head of the fastener toward and engage the inside surface of the seat ring; and (iii) the outside surface of the seat ring to engage the conical surface of the tulip, such that the cap, the rod, the seat cap, the head of the fastener, and the tulip are rigidly fixed and locked into position.

* * * * *